US011242299B2

(12) United States Patent
Khokhar et al.

(10) Patent No.: US 11,242,299 B2
(45) Date of Patent: *Feb. 8, 2022

(54) CATALYST SYSTEMS THAT INCLUDE METAL OXIDE CO-CATALYSTS FOR THE PRODUCTION OF PROPYLENE

(71) Applicant: Saudi Arabian Oil Company, Dhahran (SA)

(72) Inventors: Munir D. Khokhar, Dammam (SA); Mohammed R. Alalouni, Dammam (SA); Noor A. Sulais, Dhahran (SA); Brian Hanna, West Roxbury, MA (US); Sohel K. Shaikh, Dhahran (SA)

(73) Assignees: Saudi Arabian Oil Company, Dhahran (SA); Aramco Services Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/156,634

(22) Filed: Oct. 10, 2018

(65) Prior Publication Data

US 2020/0115299 A1 Apr. 16, 2020

(51) Int. Cl.
*B01J 23/10* (2006.01)
*C07C 6/04* (2006.01)
(Continued)

(52) U.S. Cl.
CPC ............... *C07C 6/04* (2013.01); *B01J 21/04* (2013.01); *B01J 21/08* (2013.01); *B01J 23/08* (2013.01);
(Continued)

(58) Field of Classification Search
CPC ... C07C 6/04; C07C 2523/28; C07C 2523/36; C07C 2523/30; C07C 6/02;
(Continued)

(56) References Cited

U.S. PATENT DOCUMENTS 3,442,821 A 5/1969 Hilfman
3,546,313 A 12/1970 Banks
(Continued)

FOREIGN PATENT DOCUMENTS

CN 101531558 A 9/2009
CN 102177223 A 9/2011
(Continued)

OTHER PUBLICATIONS

RU2370314, Oct. 2009, Kozlova Galina Alekseevna, translated in english.*
(Continued)

*Primary Examiner* — Smita S Patel
(74) *Attorney, Agent, or Firm* — Dinsmore & Shohl

(57) ABSTRACT

Embodiments of methods of synthesizing a metathesis catalyst system, which include impregnating tungsten oxide on silica support in the presence of a precursor to produce a base catalyst; calcining the base catalyst; impregnating a metal oxide co-catalyst comprising a metal oxide onto the surface of the base catalyst to produce a doped catalyst; and calcining the doped catalyst to produce a metathesis catalyst system. Further embodiments of processes for the production of propylene, which include contacting a hydrocarbon feedstock comprising a mixture of 1-butene and 2-butene with embodiments of the metathesis catalyst system to produce, via metathesis conversion, a product stream comprising propylene.

16 Claims, 5 Drawing Sheets

(51) Int. Cl.
  *B01J 21/04* (2006.01)
  *B01J 21/08* (2006.01)
  *B01J 23/08* (2006.01)
  *B01J 23/28* (2006.01)
  *B01J 23/30* (2006.01)
  *B01J 23/72* (2006.01)
  *B01J 23/75* (2006.01)
  *B01J 23/755* (2006.01)
  *B01J 35/10* (2006.01)
  *B01J 37/02* (2006.01)
  *B01J 37/08* (2006.01)

(52) U.S. Cl.
  CPC .............. *B01J 23/10* (2013.01); *B01J 23/28* (2013.01); *B01J 23/30* (2013.01); *B01J 23/72* (2013.01); *B01J 23/75* (2013.01); *B01J 23/755* (2013.01); *B01J 35/1019* (2013.01); *B01J 35/1023* (2013.01); *B01J 35/1042* (2013.01); *B01J 35/1047* (2013.01); *B01J 35/1061* (2013.01); *B01J 37/024* (2013.01); *B01J 37/08* (2013.01); *C07C 2521/04* (2013.01); *C07C 2521/08* (2013.01); *C07C 2523/08* (2013.01); *C07C 2523/10* (2013.01); *C07C 2523/28* (2013.01); *C07C 2523/30* (2013.01); *C07C 2523/72* (2013.01); *C07C 2523/75* (2013.01); *C07C 2523/755* (2013.01)

(58) Field of Classification Search
  CPC ............ C07C 2023/00; C07C 2523/08; C07C 2323/10; C07C 2323/16; C07C 2523/24; C07C 2523/26; C07C 2523/38; C07C 2523/40; C07C 2523/54; C07C 2523/56; C07C 2523/62; C07C 2523/63; C07C 2523/64; C07C 2523/652; C07C 2523/72; C07C 2523/755; C07C 2523/76; C07C 2523/825; C07C 2523/83; C07C 2523/84; C07C 2523/85; C07C 2523/86; C07C 2523/88; C07C 2523/883; C07C 2523/888; C07C 2521/02; C07C 2521/06; C07C 2521/04; C07C 2521/08; C07C 11/00; B01J 35/1042; B01J 35/1047; B01J 35/1061; B01J 35/1019; B01J 35/1023; B01J 35/04; B01J 35/00; B01J 35/10; B01J 2523/41; B01J 2523/68; B01J 2523/69; B01J 2523/74; B01J 23/00; B01J 23/30; B01J 35/0006; B01J 35/02; B01J 35/108; B01J 35/1052; B01J 35/1033; B01J 23/08; B01J 23/10; B01J 23/24; B01J 23/26; B01J 23/28; B01J 23/38; B01J 23/54; B01J 23/56; B01J 23/62; B01J 23/63; B01J 23/652; B01J 23/6522; B01J 23/6525; B01J 23/6527; B01J 23/683; B01J 23/686; B01J 23/687; B01J 23/755; B01J 23/76; B01J 23/83; B01J 23/825; B01J 23/85; B01J 23/86; B01J 23/866; B01J 23/888; B01J 23/89; B01J 23/896; B01J 23/8993; B01J 23/889; B01J 23/88; B01J 23/72; B01J 23/75; B01J 37/024; B01J 37/08; B01J 37/0205; B01J 37/088; B01J 37/0207; B01J 21/00; B01J 21/04; B01J 21/02; B01J 21/08; C01P 2006/12; C01P 2006/14; C01P 2006/16; C01P 2006/17
  See application file for complete search history.

(56) References Cited

U.S. PATENT DOCUMENTS

| | | |
|---|---|---|
| 3,586,731 A | 6/1971 | Heckelsberg |
| 3,702,886 A | 11/1972 | Argauer et al. |
| 3,728,415 A | 4/1973 | Arganbright |
| 4,024,201 A | 5/1977 | Takahashi |
| 4,071,471 A | 1/1978 | Banks et al. |
| 4,575,575 A | 3/1986 | Drake et al. |
| 4,609,769 A | 9/1986 | Kukes et al. |
| 5,026,935 A | 6/1991 | Leyshon et al. |
| 5,026,936 A | 6/1991 | Leyshon et al. |
| 5,191,131 A | 3/1993 | Takahata et al. |
| 5,439,859 A | 8/1995 | Durante et al. |
| 5,523,502 A | 6/1996 | Rubin |
| 6,159,433 A | 12/2000 | Chodorge et al. |
| 6,207,115 B1 | 3/2001 | Chodorge et al. |
| 6,210,562 B1 | 4/2001 | Xie et al. |
| 6,538,168 B1 | 3/2003 | Schwab et al. |
| 6,586,649 B1 | 7/2003 | Botha et al. |
| 6,646,172 B1 | 11/2003 | Schwab et al. |
| 6,777,582 B2 | 8/2004 | Gartside et al. |
| 6,977,321 B1 | 12/2005 | Dath et al. |
| 7,214,841 B2 | 5/2007 | Gartside et al. |
| 7,754,647 B2 | 7/2010 | Schubert et al. |
| 7,754,934 B2 | 7/2010 | Tsunoda et al. |
| 7,977,522 B2 | 7/2011 | Takai et al. |
| 8,299,313 B2 | 10/2012 | Takai et al. |
| 8,324,440 B2 | 12/2012 | Popp et al. |
| 8,362,308 B2 | 1/2013 | Stephan et al. |
| 8,440,874 B2 | 5/2013 | Ramachandran et al. |
| 8,586,813 B2 | 11/2013 | Ramachandran et al. |
| 8,722,568 B2 | 5/2014 | Popp et al. |
| 9,834,497 B2 | 12/2017 | Shaikh et al. |
| 9,884,794 B2 | 2/2018 | Al-Khattaf et al. |
| 2003/0176754 A1 | 9/2003 | Gartside et al. |
| 2004/0254411 A1 | 12/2004 | Steinbrenner et al. |
| 2005/0014981 A1 | 1/2005 | Gartside et al. |
| 2005/0124839 A1 | 6/2005 | Gartside et al. |
| 2006/0293548 A1 | 12/2006 | Spamer et al. |
| 2007/0038010 A1 | 2/2007 | Xie et al. |
| 2007/0225478 A1 | 9/2007 | Querci et al. |
| 2008/0171655 A1 | 7/2008 | Creyghton et al. |
| 2010/0041930 A1 | 2/2010 | Gartside et al. |
| 2010/0168487 A1 | 7/2010 | Sawyer et al. |
| 2010/0234542 A1 | 9/2010 | Blackborow et al. |
| 2011/0021858 A1 | 1/2011 | Ramachandran et al. |
| 2011/0152595 A1 | 6/2011 | Takai et al. |
| 2011/0196185 A1 | 8/2011 | Krawczyk et al. |
| 2012/0108864 A1 | 5/2012 | Gartside et al. |
| 2012/0264990 A1 | 10/2012 | Nicholas et al. |
| 2012/0283090 A1 | 11/2012 | Popp et al. |
| 2012/0289617 A1 | 11/2012 | Wang et al. |
| 2013/0085311 A1 | 4/2013 | Youn et al. |
| 2013/0165701 A1* | 6/2013 | Zhou ............... B01J 23/626 568/885 |
| 2013/0245348 A1* | 9/2013 | Vermeiren ............ C07C 6/04 585/324 |
| 2014/0148629 A1* | 5/2014 | van Hal ............... C07C 5/417 585/322 |
| 2015/0141720 A1 | 5/2015 | Ramachandran et al. |
| 2015/0141721 A1 | 5/2015 | Choi et al. |
| 2016/0130197 A1 | 5/2016 | Al-Khattaf et al. |
| 2016/0237006 A1 | 8/2016 | Stoyanova et al. |
| 2017/0001925 A1* | 1/2017 | Abudawoud ........... C07C 6/04 |
| 2017/0001926 A1 | 1/2017 | Shaikh et al. |
| 2017/0001927 A1 | 1/2017 | Al-Khattaf et al. |
| 2017/0001928 A1 | 1/2017 | Shaikh et al. |
| 2018/0057425 A1 | 3/2018 | Shaikh et al. |
| 2018/0142167 A1 | 5/2018 | Al-Ghamdi et al. |
| 2018/0208526 A1 | 7/2018 | Alshafei et al. |

(56) References Cited

U.S. PATENT DOCUMENTS

| | | | |
|---|---|---|---|
| 2018/0230071 | A1 | 8/2018 | Bonduelle et al. |
| 2019/0367432 | A1 | 12/2019 | Al-Majnouni et al. |

FOREIGN PATENT DOCUMENTS

| | | | | |
|---|---|---|---|---|
| CN | 102325742 | A | 1/2012 | |
| CN | 101531558 | B | 4/2013 | |
| CN | 102325742 | B | 7/2014 | |
| CN | 104370676 | A | 2/2015 | |
| DE | 10013253 | A1 | 9/2001 | |
| EP | 304515 | B1 | 12/1991 | |
| EP | 0920911 | A1 | 6/1999 | |
| EP | 2151424 | A1 | 2/2010 | |
| EP | 2151424 | A4 * | 5/2012 | ............ B01J 21/10 |
| GB | 1205677 | A | 9/1970 | |
| JP | 2003500190 | A | 1/2003 | |
| JP | 2012500304 | A | 1/2012 | |
| KR | 20110056510 | A | 5/2011 | |
| KR | 20130059594 | A | 6/2013 | |
| NL | 8403050 | A | 5/1986 | |
| RU | 2370314 | C1 | 10/2009 | |
| WO | 9929805 | A1 | 6/1999 | |
| WO | 00/71255 | A1 | 11/2000 | |
| WO | 2006089957 | A1 | 8/2006 | |
| WO | 2009015118 | A2 | 1/2009 | |
| WO | 2009117128 | A1 | 9/2009 | |
| WO | 2010019595 | A2 | 2/2010 | |
| WO | 2008136280 | A1 | 7/2010 | |
| WO | 2011136983 | A1 | 11/2011 | |
| WO | 2015055594 | A1 | 4/2015 | |
| WO | 2017003812 | A1 | 1/2017 | |
| WO | 2017003817 | A1 | 1/2017 | |
| WO | 2017003821 | A1 | 1/2017 | |
| WO | 2018088815 | A1 | 5/2018 | |

OTHER PUBLICATIONS

Office Action dated Apr. 5, 2019 pertaining to U.S. Appl. No. 15/873,421, filed Jan. 17, 2018, 49 pgs.

Arudra et al., "Silicalite-1 as Efficient Catalyst for Production of Propene from 1-Butene", ACS Catalysis, 2014, 4205-4212, 4, American Chemical Society.

Awayssa et al., "Modified HZSM-5 as FCC Additive for Enhancing Light Olefins Yield from Catalytic Cracking of VGO", Applied Catalysis A: General, 2014, 172-183, 477.

Balcar, et al., "Mesoporous molecular sieves as advanced supports for olefin metathesis catalysts", Coordination Chemistry Reviews 257, 2013, pp. 3107-3124, Czech Republic.

Barrett et al., "The Determination of Pore Volume and Area Distributions in Porous Substances. I. Computations from Nitrogen Isotherms", J. Am. Chem. Soc., 1951, 373-380, 73(1).

Beck et al., "A New Family of Mesoporous Molecular Sieves Prepared with Liquid Crystal Templates", J. Am. Chem. Soc., 1992, 10834-10843, 114, American Chemical Society.

Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.

Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.

Daniell et al., Enhanced Surface Acidity in Mixed Alumina-Silicas: A Low-Temperature FTIR Study:, 2000, 196, 247-260, Elsevier.

Do et al., "Zeolite Nanoclusters Coated onto the Mesopore Walls of SBA-15", J. Am. Chem. Soc., 2004, 14324-14325, 126, American Chemical Society.

International Search Report and Written Opinion dated Nov. 11, 2016 pertaining to International Application No. PCT/US2016/039025.

International Search Report and Written Opinion dated Sep. 14, 2016 pertaining to International Application No. PCT/US2016/039012.

International Search Report and Written Opinion dated Sep. 27, 2016 pertaining to International Application No. PCT/US2016/0038967.

International Search Report and Written Opinion dated Sep. 14, 2016 pertaining to International Application No. PCT/US2016/039013.

Jermy et al., "Utilization of ZSM-5/MCM-41 Composite as FCC Catalyst Additive for Enhancing Propylene Yield from VGO Cracking", J. Porous Mater, 2012, 499-509, 19, Springer.

Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.

Kumar et al., "Performance of Nano Crystalline H-ZSM-5 as Additive in FCC Catalyst: A Review", International Journal of Research in Engineering and Tehnology, May 2014, vol. 3, pp. 481-485.

Lwin et al., "Olefin Metathesis by Supported Metal Oxide Catalysts", ACS Catalysis, 2014, 2505-2520, 4, American Chemical Society.

Office Action pertaining to U.S. Appl. No. 15/190,950 dated Sep. 27, 2017.

Office Action pertaining to U.S. Appl. No. 15/190,964 dated Nov. 2, 2017.

Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.

Ruihua Gao, et al., "High-activity, single-site mesoporous WO3-MCF materials for the catalytic epoxidation of cycloocta-1,5-diene with aqueous hydrogen peroxide", Journal of Catalysis, 256, 2008, pp. 259-267, China.

Wang et al., "Synthesis and Structure of Silicalite-1/SBA-15 Composites Prepared by Carbon Templating and Crystallization", Journal of Materials Chemistry, 2007,4265-4273,17, The Royal Society of Chemistry 2007.

Wang et al., "Effect of Support Nature on WO3/SiO2 Structure and Butene-1 Metathesis", Applied Catalysis A: General, 2003, 25-37, 250, Elsevier B.V.

Zhao et al., "Effect of Tungsten Oxide Loading on Metathesis Activity of Ethene and 2-Butene Over WO3/SiO2 Catalysts" Transition Met Chem, 2009, 621-27, 34, Springer.

International Preliminary Report on Patentability dated Jan. 11, 2018—PCT/US2016/039012.

International Preliminary Report on Patentability dated Jan. 2, 2018—PCT/US2016/039012.

Non-Final Office Action pertaing to U.S. Appl. No. 15/398,196 dated Jan. 9, 2018.

Puriwat, et al., "Elucidation of the basicity dependence of 1-butene isomerization on MgO/Mg(OH)s catalysts", Catalysis Communications, 2010, pp. 80-85.

"International Search Report and Written opinion dated Mar. 28, 2018, pertaining to International Application No. PCT/US2018/013945, filed Jan. 17, 2018, 9 pages".

U.S. Office Action dated Apr. 20, 2018 pertaining to U.S. Continuation U.S. Appl. No. 15/859,794, filed Jan. 2, 2018.

International Search Report and Written Opinion dated Apr. 24, 2018 pertaining to International Application No. PCT/US2018/014131, filed Jan. 18, 2018.

Notice of Allowance dated Apr. 24, 2018 pertaining to U.S. Appl. No. 15/190,964, filed Jun. 23, 2016.

Election/Restriction Requirement dated May 21, 2018, pertaining to U.S. Appl. No. 15/866,772, filed Jan. 10, 2018.

Korean Office Action pertaining to Korea Application No. 10-2018-7003238 dated May 14, 2018 (English Translation).

(56) References Cited

OTHER PUBLICATIONS

Office Action pertaining to U.S. Appl. No. 15/866,800 dated Jun. 29, 2018.
Office Action pertaining to U.S. Appl. No. 15/190,981 dated Apr. 4, 2017.
Office Action pertaining to U.S. Appl. No. 15/866,772 dated Aug. 28, 2018.
Harmse et al., "On the Product Formation in 1-Butene Methathesis over Supported Tungsten Catalysts", Catal. Lett, vol. 137, pp. 123-131, Apr. 2010.
Shaikh et al., "Self-Methathesis of Butenes to Propylene", Catalysis in Petroleum Refining & Petrochemicals, pp. 1-6, Dec. 7-8, 2015.
DeBecker et al., "Preparation of Mo03/Si02—Al2O3 methathesis catalysts via wet impregnation with different Mo precursors", Journal of Molecular Catalysis A: Chemical , 340, pp. 65-76, 2011.
Wu et al., "Investigation on acidity of zeolites bound with silica and alumina", Studies in Surface Science and Catalysis, 143, pp. 217-225, 2002.
Examination Report pertaining to GCC Application No. 2016/31672 dated Sep. 13, 2018.
Office Action dated Jan. 31, 2019 pertaining to U.S. Appl. No. 15/866,800, filed Jan. 10, 2018 (34 pg).
Notice of Allowance dated Mar. 5, 2019 pertaining to U.S. Appl. No. 15/866,772, filed Jan. 10, 2018.
Decision of Rejection pertaining to Japanese Application No. 2017-567370 dated Sep. 4, 2019.
Office Action dated Apr. 29, 2019 pertaining to U.S. Appl. No. 16/039,983, filed Jul. 19, 2018, 36 pgs.
Yuan Guimei et al., Machine translation of CN 104370676, Feb. 2015.
Office Action dated May 2, 2019 pertaining to U.S. Appl. No. 15/859,794, filed Jan. 2, 2018, 30 pgs.
Notice of Allowance and Fee(s) Due dated Aug. 29, 2019 pertaining to U.S. Appl. No. 15/859,794, filed Jan. 2, 2018, 22 pgs.
Notice of Allowance and Fee(s) Due dated Sep. 26, 2019 pertaining to U.S. Appl. No. 15/873,421, filed Jan. 17, 2018, 30 pgs.
European Search Report for Application No. 19163840.2 dated Aug. 2, 2019.
Chinese Office Action for Application No. 201811179717.1 dated Jun. 13, 2019.
European Search Report for Application No. 16738274.6 dated Aug. 2, 2019.
Office Action dated Jun. 18, 2019 pertaining to Korean Patent Application No. 10-2018-7003251.
Office Action dated Mar. 30, 2019 pertaining to Japanese Patent Application No. 2017-567370.
Notice of Allowance and Fee(s) Due dated May 15, 2019 pertaining to U.S. Appl. No. 16/156,616, filed Oct. 10, 2018, 35 pgs.
U.S. Office Action dated Jun. 14, 2019 pertaining to U.S. Appl. No. 15/866,800, filed Jan. 10, 2018, 38 pgs.
Examination Report for Application No. GC 2018/34631 dated Aug. 22, 2019.
Notice of Allowance and Fee(s) due dated Oct. 18, 2019 pertaining to U.S. Appl. No. 16/039,983, filed Jul. 19, 2018, 29 pgs.
Machine translation claims of CN 102177223 A, Sep. 2011.
Machine translation description CN 102177223 A, Sep. 2011.
Office Action pertaining to U.S. Appl. No. 15/866,800 dated Jan. 13, 2020.
Office Action pertaining to U.S. Appl. No. 16/390,523 dated Jan. 17, 2020.
Bortnovsky et al., "Cracking of pentenes to C2-C4 light olefins over zeolites and zeotypes Role of topology and acid site strength and concentration", Applied Catalysis A: General 287, pp. 203-213, 2005.
DeBecker et al., "Aerosol route to nanostructured WO3—SiO2—Al2O3 methathesis catalysts: Toward higer propene yield", Applied Catalysis A: General 470, pp. 458-466, 2014.
Office Action pertaining to Korean Application No. 10-2019-7005618 dated Feb. 25, 2020.
International Search Report and Written Opinion pertaining to Application No. PCT/US2019/054378 dated Jan. 13, 2020.
International Search Report and Written Opinion pertaining to Application No. PCT/US2019/054377 dated Jan. 13, 2020.
Office Action dated May 27, 2020 pertaining to U.S. Appl. No. 16/156,616, filed Oct. 10, 2018, 31 pgs.
Office Action dated Jul. 24, 2020 pertaining to U.S. Appl. No. 15/866,800, filed Jan. 10, 2018, 51 pgs.
Office Action dated Jul. 14, 2020 pertaining to U.S. Appl. No. 16/390,523, filed Apr. 22, 2019, 42 pgs.
Notice of Allowance and Fee(s) Due dated Dec. 10, 2020 pertaining to U.S. Appl. No. 16/390,523, filed Apr. 22, 2019, 22 pgs.
International Search Report and Written Opinion dated Feb. 23, 2021 pertaining to International application No. PCT/US2020/058640 filed Nov. 3, 2020, 14 pgs.
Notice of Allowance and Fee(s) Due dated Oct. 19, 2020 pertaining to U.S. Appl. No. 15/866,800, filed Jan. 10, 2018, 27 pgs.
Notice of Allowance and Fee(s) Due dated Nov. 23, 2020 pertaining to U.S. Appl. No. 16/156,616, filed Oct. 10, 2018, 29 pgs.
U.S. Office Action dated Aug. 21, 2020 pertaining to U.S. Appl. No. 16/712,280, filed Dec. 12, 2019, 67 pgs.
U.S. Office Action dated Sep. 16, 2020 pertaining to U.S. Appl. No. 16/522,142, filed Jul. 25, 2019, 72 pgs.
U.S. Office Action dated Mar. 2, 2021 pertaining to U.S. Appl. No. 16/712,280, filed Dec. 12, 2019, 34 pgs.
Examination Report dated Jan. 30, 2021 pertaining to GCC Patent Application No. 2019/38446.

\* cited by examiner

CATALYST SYSTEMS THAT INCLUDE METAL OXIDE CO-CATALYSTS FOR THE PRODUCTION OF PROPYLENE

TECHNICAL FIELD

Embodiments of the present disclosure generally relate to propylene production, and more specifically relate to converting butene to propylene via metathesis using a metathesis catalyst system.

BACKGROUND

In recent years, there is a dramatic increase in the demand for propylene to feed the growing markets for polypropylene, propylene oxide and acrylic acid. Currently, most of the propylene produced worldwide is a by-product from steam cracking units, which primarily produce ethylene, or a by-product from Fluid Catalytic Cracking (FCC) units, which primarily produce gasoline. These processes cannot respond adequately to a rapid increase in propylene demand. However, the processing of lower-cost butenes co-produced by these processes gives the refiner or the petrochemical producer an opportunity to add value depending on downstream integration and relative economics. However, propylene demand growth has exceeded ethylene and gasoline and distillate demand growth, and propylene supply has not kept pace with this increase in demand.

Olefin metathesis is considered a useful reaction to shift the composition of a pool of low-value butenes to meet market demand for propylene. With new capacity coming on-stream in the Middle East and Asia, propylene production via metathesis is expected to increase.

SUMMARY

Catalytic olefin metathesis is a useful chemical reaction that is able to transform simple and cheap organic molecules into complex and valuable molecules. In olefin metathesis, two olefin molecules exchange the groups around the double bonds in the presence of a catalyst. The olefins can be of different molecules by structure and composition, or two identical molecules. In general, reaction temperatures for olefin metathesis reactions can be as low as at room temperature or can be at temperatures up to about 550° C. or greater, depending on the type of starting materials, the catalyst used, and the media in which the reaction is carried out.

However, metathesis catalysts often do not have the requisite selectivity to yield propylene and other products. Additionally, metathesis catalysts are subject to deactivation due to coking from aromatic products.

Accordingly, ongoing needs exist for metathesis catalyst systems, which allow for the selective production of propylene using butenes metathesis. Embodiments of the present disclosure are directed to the production of propylene via metathesis using metathesis catalyst systems comprising a silica support impregnated with tungsten and doped with a co-catalyst that includes a metal oxide.

Moreover, conventional metathesis catalyst systems may include a co-catalyst that is added to the base catalyst. However, in these conventional catalyst systems, simply adding the co-catalyst to the base catalyst may not produce the desired results. For example, in some conventional catalyst systems, when a co-catalyst, such as aluminum, is added to the base catalyst that includes another metal oxide, such as tungsten oxide, the metal oxide of the base catalyst may cover the aluminum co-catalyst, thereby causing a crystallite. The crystallite may then cause the catalyst system to quickly deactivate, which is costly and inefficient in propylene production applications.

Accordingly, ongoing needs exist for methods of synthesizing a metathesis catalyst system that allows for improved propylene yield and higher selectivity and conversion of 2-butene but does not produce a catalyst system that quickly deactivates. To address these needs, methods of synthesizing a metathesis catalyst system are disclosed, which may include impregnating tungsten oxide on silica support in the presence of a precursor to produce a base catalyst; calcining the base catalyst; impregnating a metal oxide co-catalyst onto the surface of the base catalyst to produce a doped catalyst; and calcining the doped catalyst to produce a metathesis catalyst system. By performing the sequential calcination and impregnation steps of this method, the produced disclosed metathesis catalyst systems do not quickly deactivate and allow for improved propylene yield and higher selectivity and conversion of 2-butene.

According to another embodiment, a process for the production of propylene is disclosed, which includes contacting a hydrocarbon feedstock comprising a mixture of 1-butene and 2-butene with embodiments of the metathesis catalyst system to produce, via metathesis conversion, a product stream comprising propylene.

Additional features and advantages of the present embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 1:
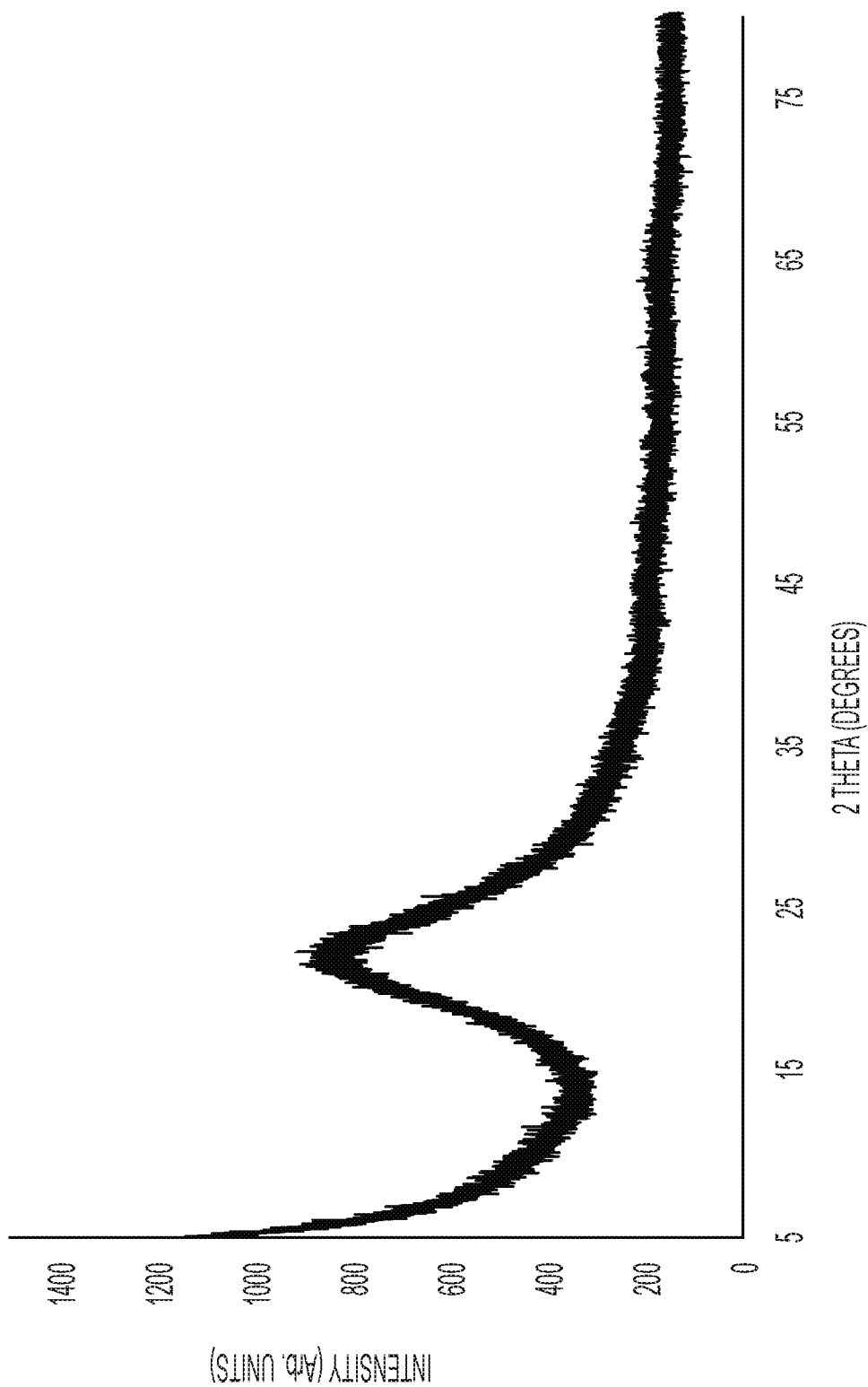
FIG. 1 is graph that illustrates the X-ray diffraction (XRD) analysis carried out for an embodiment of a large pore silica support.

Embodiments of the present disclosure are directed to systems and methods for converting a butene stream to propylene via catalyzed metathesis. As used in the application, "metathesis" is generally a two-step process: 2-butene isomerization and then cross-metathesis using the metathesis catalyst as depicted as follows in Formulas 1 and 2.

2-Butene Isomerization

Formula 1

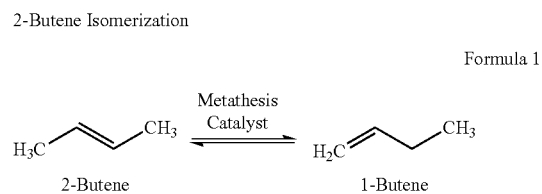

Cross-Metathesis

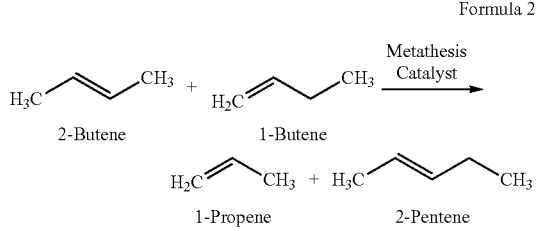

Formula 2

2-Butene + 1-Butene → 1-Propene + 2-Pentene (Metathesis Catalyst)

As shown in Formulas 1 and 2, the "metathesis" reactions are not limited to these reactants and products; however, this is the basic illustration of the reaction methodology. As shown, metathesis reactions take place between two alkene molecules. The groups bonded to the carbon atoms of the double bond are exchanged between the molecules to produce two new alkenes with the swapped groups. The specific metathesis catalyst system that is selected for the metathesis reaction helps to determine whether a cis-isomer or trans-isomer is formed, as the coordination of the olefin molecules with the metathesis catalyst system play an important role, as do the steric influences of the substituents on the double bond of the newly formed molecule.

Here, methods of synthesizing a metathesis catalyst system may include impregnating tungsten oxide on silica support in the presence of a precursor to produce a base catalyst, calcining the base catalyst, impregnating a metal oxide co-catalyst onto the surface of the base catalyst to produce a doped catalyst, and calcining the doped catalyst to produce a metathesis catalyst system. As stated previously in this disclosure, the sequential calcination and impregnation steps of this method produce embodiments of metathesis catalyst systems that do not quickly deactivate and allow for improved propylene yield and higher selectivity and conversion of 2-butene.

The metathesis catalyst system includes a base catalyst. In some embodiments; the base catalyst includes tungsten oxide impregnated on a large pore silica support in the presence of a precursor. As used in this application, "silica support" means a large pore silica catalyst that has been calcined. As used in this application "large pore" means a pore volume of at least 0.700 cm$^3$/g. In other embodiments, a silica support may have a pore volume from at least 0.700 cm$^3$/g to about 2.5 cm$^3$/g, from about 0.800 cm$^3$/g to about 2.5 cm$^3$/g, from about 0.800 cm$^3$/g to about 1.5 cm$^3$/g, from about 0.800 cm$^3$/g to about 1.25 cm$^3$/g, from about 0.800 cm$^3$/g to about 1.0 cm$^3$/g, or from about 0.850 cm$^3$/g to about 1.0 cm$^3$/g. In some embodiments, for example, the large pore silica catalyst may be a commercial spherical catalyst, such as Q-10, provided by Fuji Silysia Chemical, Ltd., which has an average pore diameter of about 10 nm, an average pore volume of about 1.00 mL/g, and a surface area of about 300 m$^2$/g.

In some embodiments, the large pore silica support may be an amorphous silica. As used in this application, "amorphous" means an amorphous silica support with a non-ordered structure and a narrow pore size distribution. This non-ordered structure may be random and thus different than the disclosed hexagonal or cubic structures of conventional silica supports. Specifically, the amorphous silica has a narrow pore size distribution of at least 3 nm to about 10 nm and a total pore volume of at least 0.700 cm$^3$/g. In other embodiments, the pore size distribution may range from at least 3 nm to about 40 nm, from about 3 nm to about 20 nm, from about 4 nm to about 10 nm, from about 4 nm to about 8 nm, or from about 4 nm to about 6 nm. In further embodiments, the total pore volume may be from at least 0.700 cm$^3$/g to about 2.5 cm$^3$/g, from about 0.800 cm$^3$/g to about 2.5 cm$^3$/g, from about 0.800 cm$^3$/g to about 1.5 cm$^3$/g, from about 0.800 cm$^3$/g to about 1.25 cm$^3$/g, from about 0,800 cm$^3$/g to about 1.0 cm$^3$/g, or from about 0.850 cm$^3$/g to about 1.0 cm$^3$/g.

As stated previously, the larger pore silica support may be prepared by placing a desired amount of a large pore silica catalyst on a ceramic plate and calcining the large pore silica catalyst. In some embodiments, the large pore silica catalyst may be calcined at a temperature of at least 100° C. In other embodiments, the large pore silica catalyst may be calcined at from about 100° C. to about 700° C., from about 100° C. to about 600° C., from about 100° C. to about 500° C., from about 100° C. to about 400° C., from about 100° C. to about 300° C., from about 100° C. to about 200° C., from about 200° C. to about 700° C., from about 200° C. to about 600° C., from about 200° C. to about 500° C., from about 200° C. to about 400° C., from about 200° C. to about 300° C., from about 300° C. to about 700° C., from about 300° C. to about 600° C., from about 300° C. to about 500° C., from about 300° C. to about 400° C., from about 400° C. to about 700° C., from about 400° C. to about 600° C., from about 400° C. to about 500° C., from about 500° C. to about 700° C., from about 500° C. to about 600° C., or from about 600° C. to about 700° C.

Additionally, in some embodiments, the large pore silica catalyst may be calcined at a temperature for at least 1 hour. In other embodiments, the large pore silica catalyst may be calcined at a temperature for about 1 hour to about 7 hours, about 1 hour to about 6 hours, about 1 hour to about 5 hours, about 1 hour to about 4 hours, about 1 hour to about 3 hours, about 1 hour to about 2 hours, for about 2 hours to about 7 hours, about 2 hours to about 6 hours, about 2 hours to about 5 hours, about 2 hours to about 4 hours, about 2 hours to about 3 hours, for about 3 hours to about 7 hours, about 3 hours to about 6 hours, about 3 hours to about 5 hours, about 3 hours to about 4 hours, for about 4 hours to about 7 hours, about 4 hours to about 6 hours, about 4 hours to about 5 hours, for about 5 hours to about 7 hours, or about 5 hours to about 6 hours, about 6 hours to about 7 hours.

Also, the large pore silica catalyst may calcined at ramping rate of at least 1° C./minute. In other embodiments, the ramping rate may be from about 1° C./minute to about 5° C./minute, from about 1° C./minute to about 4° C./minute, from about 1° C./minute to about 3° C./minute, from about 1° C./minute to about 2° C./minute, from about 2° C./minute to about 5° C./minute, from about 2° C./minute to about 4° C./minute, from about 2° C./minute to about 3° C./minute, from about 3° C./minute to about 5° C./minute, from about 3° C./minute to about 4° C./minute, or from about 4° C./minute to about 5° C./minute.

In further embodiments, the large pore silica catalyst may be calcined at multiple ramping rates and temperatures for various amounts of times to produce the large pore silica support. For example, in some embodiments of producing the silica support, the large pore silica catalyst may be calcined at 200° C. for three hours and again at 575° C. for five hours, with a ramping rate of 3° C./minute, resulting in the large pore silica support.

Without being bound by theory, the pore size distribution and pore volume of the silica support are sized to achieve better catalytic activity and reduced blocking of pores by metal oxides, whereas smaller pore volume and pore size silica supports are susceptible to pore blocking and thereby reduced catalytic activity. Reduced blocking leads to higher dispersion of metal oxide species, such as tungsten oxide, on the silica support. Higher tungsten oxide dispersion leads to higher metathesis activity and thus higher propylene yield.

The metal oxide of the base catalyst may comprise one or more oxides of a metal from the Periodic Table IUPAC Group Numbers 6-10. In one or more embodiments, the metal oxide may be an oxide of molybdenum, rhenium, tungsten, or combinations. In some embodiments, the metal oxide is tungsten oxide ($WO_3$). It is contemplated that various amounts of metal oxide may be impregnated into the silica support. For example and not by way of limitation, the molar ratio of silica to metal oxide, for example, $WO_3$, is about 1 to about 50, about 1 to about 40, about 5 to about 30, about 5 to about 15. In some embodiments, the base catalyst may include from about 5 wt. % to about 15 wt. %, about 5 wt. % to about 12 wt. %, about 5 wt. % to about 8 wt. %, about 8 wt. % to about 15 wt. %, about 8 wt. % to about 12 wt. %, or about 8 wt. % to about 10 wt. % of metal oxide based on the total weight of the base catalyst. Moreover, the metathesis catalyst system may include from about 1 to about 50% by weight, or from about 2 to about 25% by weight, or from about 5 to about 15% by weight metal oxide, for example, $WO_3$, based on the total weight of the metathesis catalyst system.

As stated previously, in some embodiments, the base catalyst includes tungsten oxide impregnated on a silica support in the presence of a precursor. A precursor may be any nonporous material that participates in a chemical reaction of the silica support to produce the metal oxide that is impregnated onto the silica support. In some embodiments, the metal precursor may be ammonium metatungstate hexahydrate. In other embodiments, the metal precursor may include tungsten chlorides. In other embodiments, the metal precursor may include tungsten hexacarbonyl.

To prepare the base catalyst, a large pore silica support may be impregnated with a metal oxide in the presence of the precursor. In some methods of impregnating the large pore silica support, the large pore silica support and water may be placed in a flask to produce a large pore silica support and water solution. In some embodiments, an amount of precursor may be weighed and mixed with the large pore silica support and water solution. The large pore silica support and water solution with precursor may then be stirred to produce a homogeneous mixture in which the precursor is dispersed in the large pore silica support. The mixture may then be rotated and heated. In some embodiments, a vacuum may be applied to the mixture to remove excess water. After vacuuming the water from the mixture, this may produce a slurry material. In some embodiments, the slurry material may be cooled to room temperature. In further embodiments, the slurry material may be dried, for example, in an oven, producing a dried material. In further embodiments, the dried material may be crushed into powder and calcined, for example, in a furnace.

In some embodiments of preparing the base catalyst, the base catalyst may be calcined after it has been impregnated with the metal oxide. In some embodiments, the base catalyst may be calcined at a temperature of at least 100° C. In other embodiments, the base catalyst may be calcined at from about 100° C. to about 700° C., from about 100° C. to about 600° C., from about 100° C. to about 500° C., from about 100° C. to about 400° C., from about 100° C. to about 300° C., from about 100° C. to about 200 from about 200° C. to about 700° C., from about 200° C. to about 600° C., from about 200° C. to about 500° C., from about 200° C. to about 400° C., from about 200° C. to about 300° C. from about 300° C. to about 700° C., from about 300° C. to about 600° C., from about 300 CC to about 500° C., from about 300° C. to about 400° C., from about 400° C. to about 700° C., from about 400° C. to about 600° C., from about 400° C. to about 500° C. from about 500° C. to about 700° C., from about 500° C. to about 600° C., or from about 600° C. to about 700° C.

Additionally, in some embodiments, the base catalyst may be calcined at a temperature for at least 1 hour. In other embodiments, the base catalyst may be calcined at a temperature for about 1 hour to about 7 hours, about 1 hour to about 6 hours, about 1 hour to about 5 hours, about 1 hour to about 4 hours, about 1 hour to about 3 hours, about 1 hour to about 2 hours, for about 2 hours to about 7 hours, about 2 hours to about 6 hours, about 2 hours to about 5 hours, about 2 hours to about 4 hours, about 2 hours to about 3 hours, for about 3 hours to about 7 hours, about 3 hours to about 6 hours, about 3 hours to about 5 hours, about 3 hours to about 4 hours, for about 4 hours to about 7 hours, about 4 hours to about 6 hours, about 4 hours to about 5 hours, for about 5 hours to about 7 hours, or about 5 hours to about 6 hours, about 6 hours to about 7 hours.

Also, the base catalyst may be calcined at ramping rate of at least 1° C./minute. In other embodiments, the ramping rate may be from about 1° C./minute to about 5° C./minute, from about 1° C./minute to about 4° C./minute, from about 1° C./minute to about 3° C./minute, from about 1° C./minute to about 2° C./minute, from about 2° C./minute to about 5° C./minute, from about 2° C./minute to about 4° C./minute, from about 2° C./minute to about 3° C./minute, from about 3° C./minute to about 5° C./minute, from about 3° C./minute to about 4° C./minute, or from about 4° C./minute to about 5° C./minute.

In further embodiments, the base catalyst may be calcined at multiple ramping rates and temperatures for various amounts of times. For example, in some embodiments of producing the base catalyst, the base catalyst may be calcined at 250° C. for two hours and at 550° C. for 8 hours, with a ramping rate of 1° C./minute until the temperature of 250° C. is reached and 3° C./minute until the temperature of 550° C. is reached, therefore producing the base catalyst.

Embodiments of the metathesis catalyst system also include a doped catalyst, which includes a metal oxide co-catalyst. In some embodiments, the metal oxide co-catalyst may include a transition metal. In further embodiments, the metal oxide co-catalyst includes one or more metals selected from copper (Cu), cobalt (Co), cerium (Ce), nickel (Ni), gallium (Ga), aluminum (Al), and molybdenum (Mo). It is contemplated that various amounts of metal oxide co-catalyst may be impregnated onto the large pore silica support. In some embodiments, the metathesis catalyst system may comprise at least 0.5 weight percent (wt. %) metal oxide co-catalyst based on the total weight of the metathesis catalyst system. In further embodiments, metathesis catalyst system may comprise from about 0.5 wt. % to about 5 wt. % co-catalyst, from about 0.5 wt. % to about 4 wt. % co-catalyst, from about 0.5 wt. % to about 3 wt. % co-catalyst, from about 0.5 wt. % to about 2 wt. % co-catalyst, from about 0.5 wt. % to about 1 wt. % co-catalyst, from about 1 wt. % to about 5 wt. % co-catalyst, from about 1 wt. % to about 4 wt. % co-catalyst, from about 1 wt. % to about 3 wt. % co-catalyst, from about 1 wt. % to about 2 wt. % co-catalyst, from about 2 wt. % to about 5 wt. % co-catalyst, from about 2 wt. % to about 4 wt. % co-catalyst, from about 2 wt. % to about 3 wt. % co-catalyst, from about 3 wt. % to about 5 wt. % co-catalyst, from about 3 wt. % to about 4 wt.

% co-catalyst, or from about 4 wt. % to about 5 wt. % co-catalyst based on the total weight of the metathesis catalyst system.

To prepare the doped catalyst, a base catalyst may be prepared as previously described, and a metal oxide co-catalyst may be dispersed onto the base catalyst. In some embodiments, the solid metal-based co-catalyst may be dispersed by a liquid impregnation method. In embodiments of a liquid impregnation method, a metal oxide co-catalyst is impregnated on a silica support via a liquid in the presence of one or more precursors. As stated previously, a precursor may be any nonporous material that participates in a chemical reaction to impregnate the metal oxide co-catalyst onto the silica support. In some embodiments, the metal precursor may be one or more of tungsten (V) chloride, copper (II) chloride, cobalt (III) chloride, cerium (III) nitrate hexahydrate, nickel (II) chloride, gallium trichloride, aluminium chloride, molybdenum (V) chloride, copper (IT) nitrate hydrate, cobalt (II) nitrate hexahydrate, cerium acetylacetonate hydrate, nickel nitrate, gallium (III) nitrate hydrate, aluminium nitrate nonahydrate, and ammonium molybdate. In some wet impregnating methods, the base catalyst and water may be placed in a flask to produce a base catalyst and water solution. In some embodiments, an amount of precursor may be weighed and mixed with the base catalyst and water solution. The base catalyst and water solution with precursor may then be stirred to produce a homogeneous mixture in which the precursor is dispersed in the base catalyst. The mixture may then be rotated and heated. In some embodiments, a vacuum may be applied to the mixture to remove excess water. After vacuuming the water from the mixture, this may produce a slurry material. In some embodiments, the slurry material may be cooled to room temperature. In further embodiments, the slurry material may be dried, for example, in an oven, producing a dried material. In further embodiments, the dried material may be crushed into powder and calcined, for example, in a furnace.

Once the large pore silica support has been impregnated with the tungsten oxide and the metal oxide co-catalyst, a doped catalyst is produced. In some embodiments, the doped catalyst is further calcined to produce the metathesis catalyst system. The doped catalyst may be calcined at a temperature for at least 1 hour. In other embodiments, the base catalyst may be calcined at a temperature for about 1 hour to about 7 hours, about 1 hour to about 6 hours, about 1 hour to about 5 hours, about 1 hour to about 4 hours, about 1 hour to about 3 hours, about 1 hour to about 2 hours, for about 2 hours to about 7 hours, about 2 hours to about 6 hours, about 2 hours to about 5 hours, about 2 hours to about 4 hours, about 2 hours to about 3 hours, for about 3 hours to about 7 hours, about 3 hours to about 6 hours, about 3 hours to about 5 hours, about 3 hours to about 4 hours, for about 4 hours to about 7 hours, about 4 hours to about 6 hours, about 4 hours to about 5 hours, for about 5 hours to about 7 hours, or about 5 hours to about 6 hours, about 6 hours to about 7 hours.

Also, the doped catalyst may be calcined at ramping rate of at least 1° C./minute. In other embodiments, the ramping rate may be from about 1° C./minute to about 5° C./minute, from about 1° C./minute to about 4° C./minute, from about 1° C./minute to about 3° C./minute, from about 1° C./minute to about 2° C./minute, from about 2° C./minute to about 5° C./minute, from about 2° C./minute to about 4° C./minute, from about 2° C./minute to about 3° C./minute, from about 3° C./minute to about 5° C./minute, from about 3° C./minute to about 4° C./minute, or from about 4° C./minute to about 5° C./minute.

In further embodiments, the doped catalyst may be calcined at multiple ramping rates and temperatures for various amounts of times. For example, in some embodiments of producing the metathesis catalyst system, the doped catalyst may be calcined at 250° C. for two hours and at 550° C. for 8 hours, with a ramping rate of 1° C./minute until the temperature of 250° C. is reached and 3° C./minute until the temperature of 550° C. is reached, therefore producing the base catalyst.

In further embodiments, the doped catalyst may be calcined at multiple ramping rates and temperatures for various amounts of times. For example, in some embodiments of producing the metathesis catalyst system, the doped catalyst may be calcined at 250° C. for two hours and at 550° C. for 8 hours, with a ramping rate of 1° C./minute until the temperature of 250° C. is reached and 3° C./minute until the temperature of 550° C. is reached, therefore producing the metathesis catalyst system.

The metathesis catalyst system may comprise at least 0.5 weight percent (wt. %) co-catalyst based on the total weight of the metathesis catalyst system. In further embodiments, metathesis catalyst system may comprise from about 0.5 wt. % to about 5 wt. % co-catalyst, from about 0.5 wt. % to about 4 wt. % co-catalyst, from about 0.5 wt. % to about 3 wt. % co-catalyst, from about 0.5 wt. % to about 2 wt. % co-catalyst, from about 0.5 wt. % to about 1 wt. % co-catalyst, from about 1 wt. % to about 5 wt. % co-catalyst, from about 1 wt. % to about 4 wt. % co-catalyst, from about 1 wt. % to about 3 wt. % co-catalyst, from about 1 wt. % to about 2 wt. % co-catalyst, from about 2 wt. % to about 5 wt. % co-catalyst, from about 2 wt. % to about 4 wt. % co-catalyst, from about 2 wt. % to about 3 wt. % co-catalyst, from about 3 wt. % to about 5 wt. % co-catalyst, from about 3 wt. % to about 4 wt. % co-catalyst, or from about 4 wt. % to about 5 wt. % co-catalyst based on the total weight of the metathesis catalyst system.

Additionally, other optional components may be included into the metathesis catalyst system. Without being bound by theory, other optional components may aid in the uniform dispersion of the metal onto the surface of silica during the synthesis process. For example, the metathesis catalyst may include a structuring agent. In one embodiment, the structuring agent is a tri-block copolymer structuring agent. In a further embodiment, the tri-block copolymer structuring agent is a poly(ethylene glycol)-block-poly(propylene glycol) block-polyethylene glycol) structure, which may be also called a poloxamer structure. One suitable commercial embodiment of the surfactant tri-block copolymer structuring agent is Pluronic® P123 by BASF Corporation.

The metathesis catalyst system has a total acidity from about 0.125 millimole/gram (mmol/g) to about 0.500 mmol/g. Without being bound by theory, if the material exceeds 0.500 mmol/g, other detrimental side reactions may result, such as cracking and hydrogen transfer reactions. In further embodiments, the metathesis catalyst system may have a total acidity from about 0.125 mmol/g to about 0.250 mmol/g, or from about 0.125 mmol/g to about 0.150 mmol/g.

While various surface areas are contemplated, the metathesis catalyst system may, in one or more embodiments, have a surface area of at least about 400 meters/gram (m$^2$/g), or from about 400 m$^2$/g about 800 m$^2$/g, or from about 400 m$^2$/g to about 500 m$^2$/g, or from about 400 m$^2$/g to about 450 m$^2$/g, or from about 425 m$^2$/g to about 450 m$^2$/g.

The metathesis catalyst system has a pore size distribution of pore size distribution of at least 3 nm to about 40 nm. In other embodiments, the pore size distribution may range from at least 3 nm to about 40 nm, from about 3 nm to about 20 nm, from about 4 nm to about 10 nm, from about 4 nm to about 8 nm, or from about 4 nm to about 6 nm.

The metathesis catalyst system has a total pore volume of at least 0.700 cm$^3$/g. In further embodiments, the total pore volume may be from at least 0.700 cm$^3$/g to about 2.5 cm$^3$/g, from about 0.800 cm$^3$/g to about 2.5 cm$^3$/g, from about 0.800 cm$^3$/g to about 1.5 cm$^3$/g, from about 0.800 cm$^3$/g to about 1.25 cm$^3$/g, from about 0.800 cm$^3$/g to about 1.0 cm$^3$/g, or from about 0.850 cm$^3$/g to about 1.0 cm$^3$/g.

In operation, a hydrocarbon feedstock comprising a mixture of 1-butene and 2-butene is contacted with embodiments of the metathesis catalyst system to produce, via metathesis conversion, a product stream comprising propylene. The hydrocarbon feedstock comprises a mixture of 1-butene and 2-butene, and optionally comprises one or more isomers, such as trans-2-butene and cis-2-butene. In some embodiments, the hydrocarbon feedstock comprises more 2-butene than 1-butene. The present discussion is specifically directed to butene-based hydrocarbon feedstock streams; however, it is known that other $C_1$-$C_6$ components may also be present in the hydrocarbon feedstock stream. As shown previously, metathesis involves isomerization of 2-butene to 1-butene followed by cross-metathesis of the 2-butene and 1-butene into a metathesis product stream comprising propylene, and other alkenes and alkanes such as pentane.

Various operating conditions are contemplated for the contacting of the hydrocarbon feedstock with the metathesis catalyst system. For example, the hydrocarbon feedstock may contact the metathesis catalyst system at a space hour velocity of about 10 to about 10,000 hr$^{-1}$ or about 300 to about 1200 hr$^{-1}$. Moreover, the hydrocarbon feedstock may contact the metathesis catalyst system at a temperature of about 200° C. to about 600° C., or about 300° C. to about 600° C., or about 400° C. to about 600° C., or about 400° C. to about 550° C., or about 450° C. to about 600° C., or about or about 450° C. to about 550° C. Furthermore, the hydrocarbon feedstock may contact the metathesis catalyst system at a pressure of about 1 to about 30 bars, or about 1 to about 10 bars.

Optionally, the metathesis catalyst system may, in some embodiments, be pretreated prior to metathesis. For example, the metathesis catalyst may be pretreated with $N_2$ for about 1 hour to about 5 hours before metathesis at a temperature of at least about 400° C., or at least about 500° C.

Without being bound by theory, it is desired that the aromatics yield be low as it causes coke formation, which can lead to catalyst deactivation. Without being bound by theory, the improved propylene yield and reduced side reactions is due in part to the high selectivity of the isomerization from 2-butene to 1-butene. Moreover, by increasing the yield of 1-butene via isomerization, the subsequent cross-metathesis of 2-butene and 1-butene is able to yield more propylene in the product stream. For example, in some embodiments, the propylene yield for processes that utilize the metathesis catalyst systems may be at least 10%. In other embodiments, the propylene yield may be from about 10% to about 60%, about 10% to about 50%, about 10% to about 40%, about 10% to about 30%, about 10% to about 20%, about 20% to about 60%, about 20% to about 50%, about 20% to about 40%, about 20% to about 30%, about 30% to about 60%, about 30% to about 50%, about 30% to about 40%, about 40% to about 60%, about 40% to about 50%, or about 50% to about 60% for processes that utilize the metathesis catalyst systems.

As will be demonstrated in the examples which follow, methods using the metathesis catalyst system show a higher 2-butene conversion and better propylene yield compared to conventional metathesis catalysts. Reiterating the prior statements, the selective isomerization of 2-butene to 1-butene and less hydrogen transfer reactions (less aromatics formation) are additional advantages of the metathesis catalyst systems compared to conventional metathesis catalysts. The formation of undesirable isobutylene is also reduced in the metathesis catalyst systems compared to conventional metathesis catalysts.

Test Methods

Determination of "Conversion" was calculated according to Formula 1, where $n_i$ is the number of moles of component "i" (2-butenes) entering or leaving the reactor.

$$\text{Conversion} = \frac{n_{i,in} - n_{i,out}}{n_{i,in}} \times 100 \tag{1}$$

Similarly, determination of "Conversion $C_4$" was calculated according to Formula 2.

$$\text{Conversion } C_4 = 100 - (\text{Cis Butene Yield} + \text{Trans Butene Yield} + \text{iso Butene Yield} + \text{1-Butene Yield}) \tag{2}$$

Determination of "Selectivity" was calculated according to Formula 3.

$$\text{Selectivity} = \frac{\text{Yield of Product}}{\text{Conversion}} \times 100 \tag{3}$$

The surface area of the samples was measured by nitrogen adsorption at 77 Kelvin (K) using AUTOSORB-1 (Quanta Chrome). Before adsorption measurements, samples (ca. 0.1 g) were heated at 220° C. for 2 hours under nitrogen flow. The nitrogen adsorption isotherms of catalysts were measured at liquid nitrogen temperature (77 K). The surface areas were calculated by the Brunauer Emmett-Teller (BET) method. The total relative pore volume was estimated from the amount of N2 adsorbed at P/P0=0.99. Barret E P, Joyner L J, Halenda P H, J. Am. Chem. Soc. 73 (1951) 373-380. The percent improvement is equal to the difference between the improved value and the initial value divided by the initial value. The quotient is then multiplied by 100 to convert the improvement to percent improvement. The initial value could also be a reference value.

EXAMPLES

The following examples illustrate one or more additional features of the present disclosure. It should be understood that these examples are not intended to limit the scope of the disclosure or the appended claims in any manner.

To compare the effect of the metathesis catalyst system on propylene production, samples of metathesis catalyst systems were prepared and tested under various process conditions.

Preparation of the Large Pore Silica Support

A large pore silica support was prepared by placing a 50 grams of a large pore silica catalyst on a ceramic plate. Here, the large pore silica catalyst was a commercial spherical catalyst, Q-10, provided by Fuji Silysia Chemical, Ltd. The commercial spherical catalyst had an average pore diameter of about 10 nm, an average pore volume of about 1.00 mL/g, and a surface area of about 300 m$^2$/g. The spherical catalyst was then calcined at 200° C. for three hours and again at 575° C. for five hours, with a ramping rate of 3° C./minute, resulting in the large pore silica support.

Preparation of the Base Catalyst (in the Inventive Examples): The Comparative Example In a typical synthesis of the base catalyst, samples of a large pore silica support were impregnated with a metal oxide in the presence of the precursor. Here, the metal oxide was tungsten oxide. To prepare the base catalyst, 50 grams of the large pore silica support were placed in a 500 mL round-bottom flask and 200 mL of deionized water were added to the large pore silica support to produce a large pore silica support and water solution. Then, approximately 5.896 grams of precursor, which was ammonium metatungstate hydrate 99.99% trace metals basis, was weighed and mixed with the large pore silica support and water solution. The large pore silica support and water solution with precursor was then stirred for about 30 minutes at 400 rotations per minute (RPM) to produce a homogeneous mixture in which the precursor was dispersed in the large pore silica support. The flask was then placed in on vacuum rotary evaporator where the mixture was rotated and heated at 80° C. using a water bath. Then, a vacuum was applied to the mixture to remove excess water, producing a slurry material. After vacuuming the water from the solution, the slurry material was left in the flask, which was cooled to room temperature and subsequently dried overnight at 80° C. in an oven. The following day, the dried material was crushed into powder and left for calcination in a furnace. The material was calcined at 250° C. for 2 hours and at 550° C. for 8 hours, with a ramping rate of 1° C./minute until the first temperature is reached and 3° C./minute until the second temperature was reached, therefore producing the base catalyst. The metal loading was calculated to be 10 wt % $WO_3/SiO_2$.

The surface area and pore volume of the silica support and base catalyst were analyzed using an Autosorb iQ2 from Quantachrome Instruments. The measured BET surface area and pore volume are provided in Table 1.

TABLE 1

BET Surface Area Analysis for Blank Silica and Tungsten Loaded Silica.

| Example | BET Surface Area ($m^2/g$) | Pore Volume ($cm^3/g$) |
|---|---|---|
| 100 wt. % Si Blank (Large Pore Silica Support) | 304.41 | 1.13 |
| 10 wt. % $WO_3/SiO_2$ (Comparative Example) | 274.35 | 0.81 |

The X-ray Diffraction (XRD) for the silica support was carried out after calcining at 200° C. for three hours and then at 575° C. for five hours, with a ramping rate of 3° C./minute. As shown in FIG. 1, the XRD shows a simple amorphous structure, characterized by the peak in the 2θ range from 18° to 30°.

Figure 2:
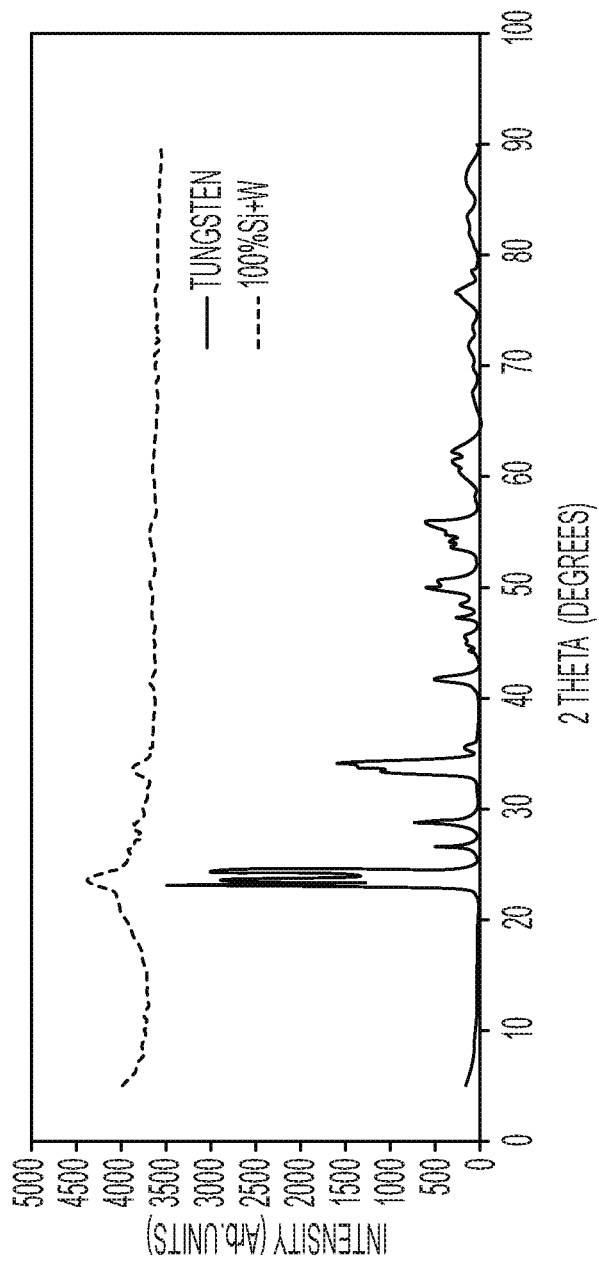
FIG. 2 is a graph that illustrates the XRD analysis of tungsten oxide versus a 10 wt. % $WO_3/SiO_2$ base catalyst denoted by dotted and solid lines, respectively.
Figure 3:
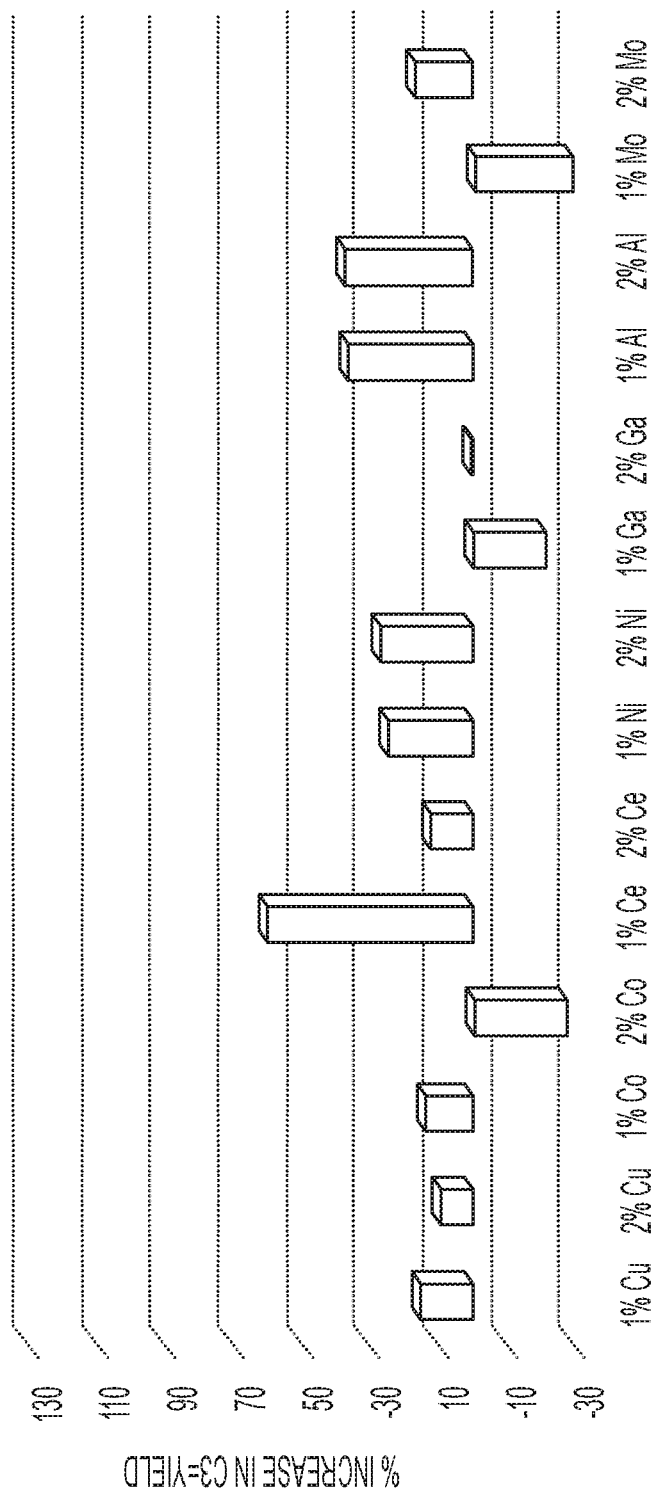
FIG. 3 is a graph illustrating the effect of weight percent of the co-metal in embodiments of the metathesis catalyst system on propylene yield at 450° C.

FIG. 2 shows the XRD of blank tungsten oxide compared to the XRD of the Comparative Example. The red diffraction graph shows the characteristic peaks of crystalline $WO_3$ which are in line with the Joint Committee on Powder Diffraction Standards card No. 00-005-0364 with the monoclinic crystal structure. The blue diffraction graph demonstrates the XRD pattern of the blank silica support with 10 wt % tungsten on it. After loading tungsten oxide on the silica support's surface, the structure of the silica morphology holds. This is because the tungsten oxide is finely dispersed on the surface of the silica support.

Preparation of the Metathesis Catalyst System: The Inventive Examples A-G

To prepare the Inventive Examples, the base catalyst was doped with a metal oxide co-catalyst to produce a doped catalyst, and then the doped catalyst was calcined to produce the final inventive examples of the metathesis catalyst system. To produce the doped catalyst, copper, cobalt, cerium, nickel, gallium, aluminum, and molybdenum metals were doped onto the base catalyst using a wet impregnation method. The metal precursors used to impregnate the base catalyst were all in soluble form. Metal nitrates (precursors) were dissolved in water based on the pore volume of the base catalyst calculated from the BET Surface area data (Table 1) to obtain samples having 1 wt % or 2 wt. % co-catalyst. The calculation was based on the total weight percentage of the base catalyst. In the wet impregnation method, five drops of the metal nitrates precursor solution were added drop-wise to the base catalyst. A glass rod was used to thoroughly mix the solution and the base catalyst. The precursors and their amount dissolved in water are listed in Table 2.

TABLE 2

Amounts of Co-Metals and Precursors.

| Example | Co-Metal | Weight Percent of Co-Metal (wt. %) | Precursor | Amount of Precursor (grams) |
|---|---|---|---|---|
| Inv. A-1 | Cu | 1 | Copper (II) nitrate hydrate | 0.11 |
| Inv. A-2 | Cu | 2 | Copper (II) nitrate hydrate | 0.23 |
| Inv. B-1 | Co | 1 | Cobalt (II) nitrate hexahydrate | 0.06 |
| Inv. B-2 | Co | 2 | Cobalt (II) nitrate hexahydrate | 0.12 |
| Inv. C-1 | Ce | 1 | Cerium acetylacetonate hydrate | 0.12 |
| Inv. C-2 | Ce | 2 | Cerium acetylacetonate hydrate | 0.25 |
| Inv. D-1 | Ni | 1 | Nickel nitrate | 0.195 |
| Inv. D-2 | Ni | 2 | Nickel nitrate | 0.389 |
| Inv. E-1 | Ga | 1 | Gallium (III) nitrate hydrate | 0.136 |
| Inv. E-2 | Ga | 2 | Gallium (III) nitrate hydrate | 0.273 |
| Inv. F-1 | Al | 1 | Aluminum nitrate nonahydrate | 0.368 |
| Inv. F-2 | Al | 2 | Aluminum nitrate nonahydrate | 0.680 |
| Inv. G-1 | Mo | 1 | Ammonium molybdate | 0.07 |
| Inv. G-2 | Mo | 2 | Ammonium molybdate | 0.153 |

Following that, the mixture was placed in a drying oven overnight at 80° C. Finally, to prepare the final samples of the metathesis catalyst system, each doped catalyst sample was placed in a drying oven overnight at 80° C. The dried, doped catalyst was calcined at 250° C. for 2 hours and at 550° C. for 8 hours, with a ramping rate of 1° C./minute until the first temperature (250° C.) was reached and 3° C./minute until the second temperature (550° C.) was reached, resulting in samples of the metathesis catalyst system, Metathesis Catalyst System Evaluation The prepared catalysts were tested for their activity and selectivity to the butenes metathesis reaction in a fixed bed continuous flow reactor (ID 0.25 in, Autoclave Engineers, Ltd.) at atmospheric pressure. Fixed amount of catalyst samples, 1 mL of each Comparative or Inventive Example was packed in the reactor tube with 1 mL Grade 20 Silicon Carbide at the bottom of the reactor, for a total of 2 mL.

The catalysts were pretreated under $N_2$ at 550° C. for 150 minutes. All reactions were carried out at three temperatures of 450° C. 500° C. and 550° C. and atmospheric pressure. At each temperature point, the reaction was held for 3.5 hours.

A gas hourly space velocity (GHSV) of 900 was maintained using 2-butene (5 mL/min) as feed with nitrogen as diluent (25 mL/min). The quantitative analysis of the reaction products were carried out on-line using an Agilent GC-7890B with an FID equipped with HP-Al/KCL (50 m×0.53 mm×15 microns) Column.

The following paragraphs provide the propylene yield, selectivity and 2-butene conversion for each of the Comparative and Inventive Examples at 450° C., 500° C., and 550° C., respectively.

Figure 4:
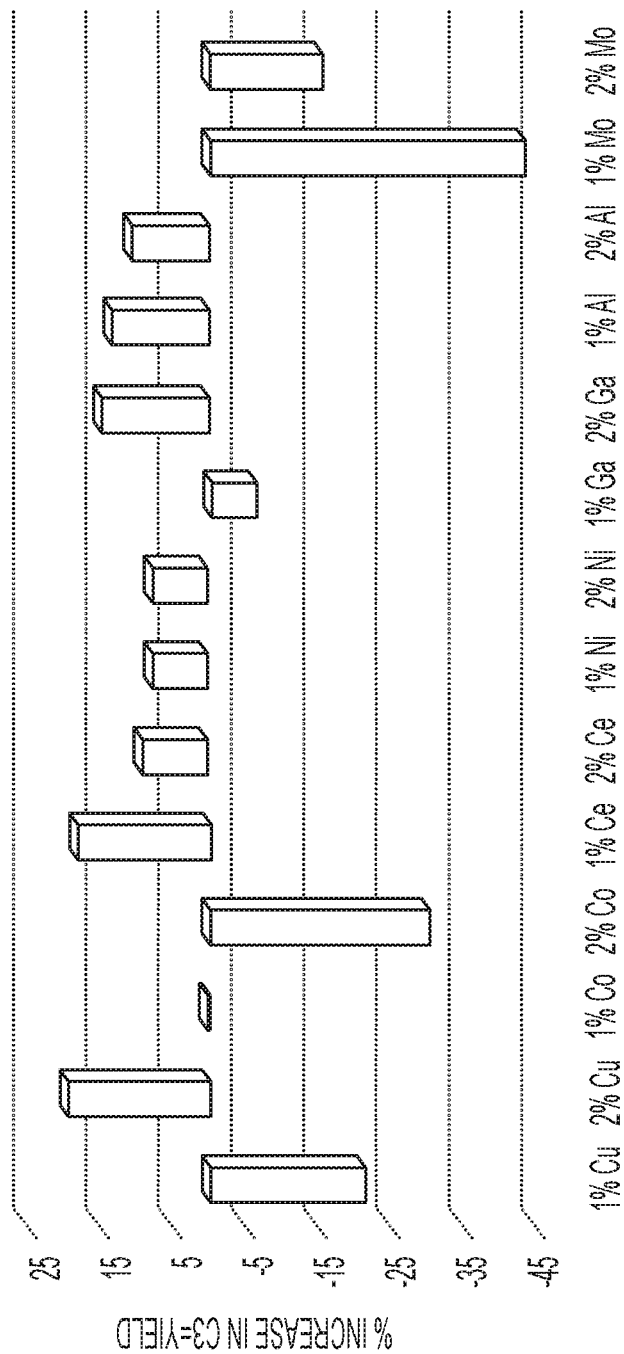
FIG. 4 is a graph illustrating the effect of weight percent of the co-metal on propylene yield at 500° C.
Figure 5:
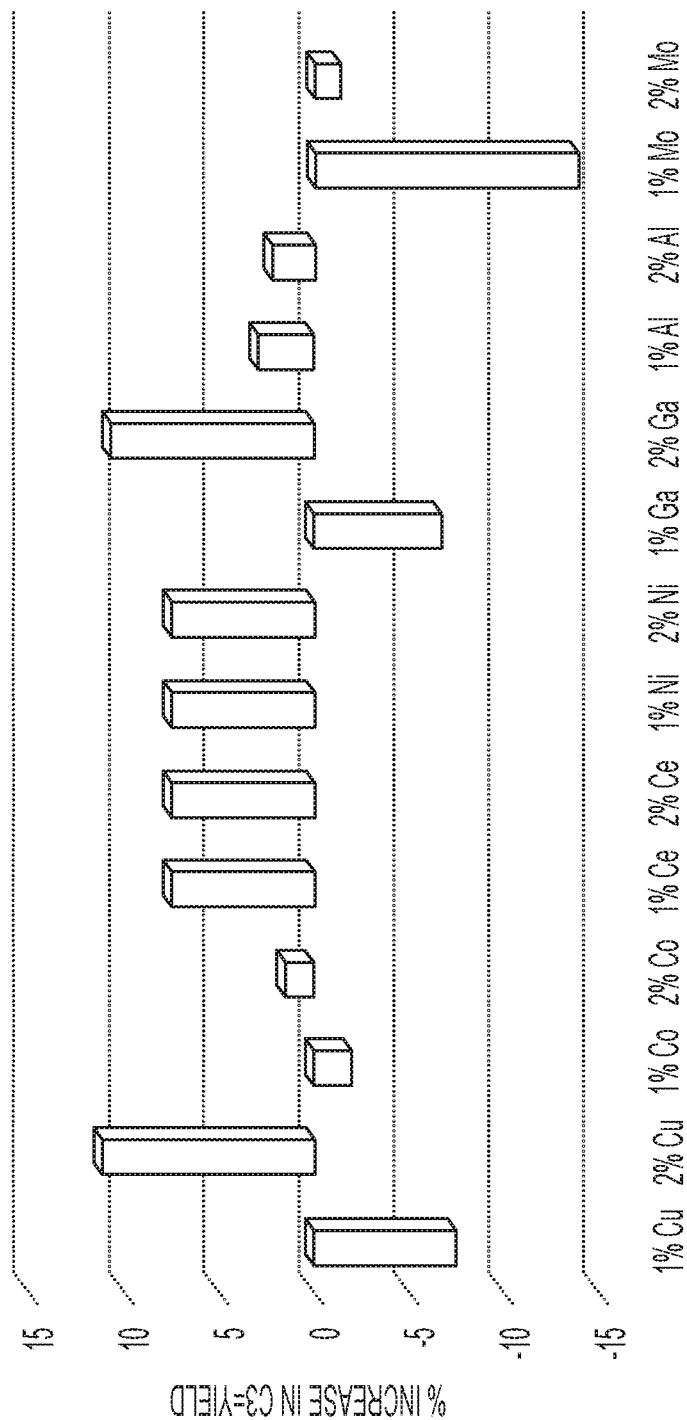
FIG. 5 is a graph illustrating the effect of weight percent of the co-metal on propylene yield at 550° C.

After screening each of the Comparative and Inventive Examples, it was observed that some co-metals allowed for a higher activity for conversion, propylene yield, and selectivity at various temperatures. FIGS. 4, 5, and 6 illustrate these results, and the subsequent paragraphs will discuss the trends that were observed from the results.

For the Inventive Examples containing copper in the metal oxide co-catalyst, Inv. A-1 and Inv. A-2, it was observed that at 450° C., inv. A-2 showed improved conversion (63.93% compared to 60%), yield (21.76% compared to 19.9%), and selectivity (34.04% compared to 33.17%). At 500° C., Inv. A-2 also showed improved conversion (79.92% compared to 72.34%), yield (29.23% compared to 24.4%), and selectivity (36.57% compared to 33.72%). Finally, at 550° C., inv. A-1 showed improved yield (25.71% compared to 27.9%) and selectivity (33.75% compared to 35.54%), and inv. A-2 showed improved conversion (83.72% compared to 78.56%), yield (30.98% compared to 27.9%) and selectivity (37.00% compared to 35.54%).

For the Inventive Examples containing cobalt in the metal oxide co-catalyst, Inv. B-1 and Inv. B-2, it was observed that at 450° C., inv. B-1 showed improved conversion (67.71% compared to 60%), yield (22.63% compared to 19.9%), and selectivity (33.42% compared to 33.17%, and Inv. B-2 showed improved selectivity (35.14% compared to 33.17%). At 500° C., Inv. B-1 also showed improved conversion (72.76% compared to 72.34%), yield (24.54% compared to 24.4%), and selectivity (33.73% compared to 33.72%), and inv. B-2 showed improved selectivity (35.30% compared to 33.72%). Finally, at 550° C., Inv. B-2 showed improved conversion (78.75% compared to 78.56%), yield (28.23% compared to 27.9%) and selectivity (35.85% compared to 35.54%).

For the Inventive Examples containing cerium in the metal oxide co-catalyst, Inv. C-1 and Inv. C-2, it was observed that at 450° C., both examples Inv. C-1 and Inv. C-2 showed improved conversion (82.17% and 60.51%, respectively, compared to 60%), yield (31.83% and 22.36%, respectively, compared to 19.9%), and selectivity (38.74% and 36.95%, respectively, compared to 33.17%). At 500° C., both Inv. C-1 and C-2 showed improved conversion (82.13% and 75.29%, respectively, compared to 72.34%), yield (28.87% and 26.72%, respectively, compared to 24.4%), and selectivity (35.15% and 35.49%, respectively, compared to 33.72%). Finally, at 550° C., both inv. C-1 and C-2 showed improved conversion (81.25% and 81.23%, respectively, compared to 78.56%), yield (29.79% and 29.92%, respectively, compared to 27.9%) and selectivity (36.66% and 36.83%, respectively, compared to 35.54%).

For the Inventive Examples containing nickel in the metal oxide co-catalyst, inv. D-1 and Inv. D-2, it was observed that at 450° C., both examples inv. D-1 and Inv. D-2 showed improved conversion (60.84% and 62.28%, respectively, compared to 60%), yield (24.91% and 25.36%, respectively, compared to 19.9%), and selectivity (40.94% and 40.72%, respectively, compared to 33.17%). At 500° C., both Inv. D-1 and D-2 showed improved yield (26.35% and 26.4%, respectively, compared to 24.4%) and selectivity (36.59% and 36.59%, respectively, compared to 33.72%). Finally, at 550° C., both inv. D-1 and D-2 showed improved conversion (81.12% and 81.23%, respectively, compared to 78.56%), yield (29.84% and 29.84%, respectively, compared to 27.9%) and selectivity (36.79% and 36.69%, respectively, compared to 35.54%).

For the Inventive Examples containing gallium in the metal oxide co-catalyst, inv. E-1 and Inv. E-2, it was observed that at 450° C., Inv. E-2 showed improved conversion (62.51% compared to 60%) and yield (20.15% compared to 19.9%). At 500° C., inv. E-2 showed improved conversion (81.68% compared to 72.34%), yield (28% compared to 24.4%), and selectivity (34.28% compared to 33.72%). Finally, at 550° C., Inv. E-1 showed improved selectivity (39.60% compared to 35.54%), and E-2 showed improved conversion (87.15% compared to 78.56%) and yield (30.77% compared to 27.9%).

For the inventive Examples containing aluminum in the metal oxide co-catalyst, Inv. F-1 and inv. F-2, it was observed that at 450° C., both examples Inv. F-1 and Inv. F-2 showed improved conversion (79.1% and 81.65%, respectively, compared to 60%), yield (27.21% and 27.33%, respectively, compared to 19.9%), and selectivity (34.40% and 33.47%, respectively, compared to 33.17%). At 500° C., both Inv. F-1 and F-2 showed improved conversion (85.94% and 86.1%, respectively, compared to 72.34%) and yield (27.7% and 27.06%, respectively, compared to 24.4%). Finally, at 550° C., both Inv. F-1 and F-2 showed improved conversion (86.34% and 86.64%, respectively, compared to 78.56%) and yield (28.75% and 28.54%, respectively, compared to 27.9%).

For the Inventive Examples containing molybdenum in the metal oxide co-catalyst. Inv. G-1 and Inv. G-2, it was observed that at 450° C., Inv. G-1 showed improved selectivity (36.31% compared to 33.17%), and Inv. G-2 showed improved conversion (65.5% compared to 60%), yield (23.35% compared to 19.9%), and selectivity (35.65% compared to 33.17%). Also, at 550° C., Inv. G-1 showed improved selectivity (35.77% compared to 35.54%).

One advantage that is apparent from these results is that using a metal oxide co-catalyst on the base catalyst would boost the conversion, propylene yield, or selectivity for at least one of each of the embodiments at various temperatures. Overall, it may be apparent that propylene yield was generally higher for the Inventive Examples at lower reaction temperatures. As the temperatures increased, a decrease in propylene yield was observed, which could be a result of the reaction reaching an equilibrium state of electronic transition. Moreover at higher temperature unwanted side products formation could may lead to a decrease in propylene yield as well.

From these results, it may be apparent that using a metal oxide co-catalyst on the base catalyst (the disclosed metathesis catalyst system) would boost the conversion, propylene yield, or selectivity compared to conventional catalyst systems (the base catalyst without a co-metal). Therefore, the disclosed metathesis catalyst systems are commercially advantageous compared to existing or known metathesis processes for propylene production—such as those that use only a tungsten oxide silica catalyst (the base catalyst, or "the Comparative Example).

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition or formulation should be appreciated as containing, in some embodiments, a mixture of isomers of that constituent. It should be appreciated that the examples supply compositional ranges for various compositions, and that the total amount of isomers of a particular chemical composition can constitute a range.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

What is claimed is:

1. A method of synthesizing a metathesis catalyst system comprising:
    impregnating a metal oxide onto a large pore silica support in a presence of a precursor to produce a base catalyst comprising a metal oxide;
    calcining the base catalyst at a first temperature for a first time period and a second temperature for a second time period;
    impregnating from about 0.5 wt. % to about 2.5 wt. % of a metal oxide co-catalyst, based on a total weight of the metathesis catalyst system, onto the base catalyst to produce a doped catalyst, wherein the metal oxide co-catalyst comprises Ce, Ni, or both Ce and Ni; and
    calcining the doped catalyst at a third temperature for a third time period and a fourth temperature for a fourth time period to produce the metathesis catalyst system.

2. The method of claim 1, wherein the large pore silica support comprises an amorphous silica.

3. The method of claim 1, wherein the base catalyst comprises from about 8 wt. % to about 12 wt. % tungsten oxide, based on a total weight of the base catalyst.

4. The method of claim 1, wherein the precursor comprises ammonium metatungstate hexahydrate.

5. The method of claim 1, wherein the metathesis catalyst system has one or more of a surface area of about 400 $m^2/g$ to about 800 $m^2/g$, a pore size distribution of about 3 nm to about 40 nm, and a total pore volume of at least 0.700 $cm^3/g$ to about 2.5 $cm^3/g$.

6. The method of claim 1, wherein the metal oxide co-catalyst comprises Ce.

7. The method of claim 1, wherein the metal oxide co-catalyst comprises Ni.

8. The method of claim 1, wherein the first temperature and the third temperature are 250° C.

9. The method of claim 1, wherein the second temperature and the fourth temperature are 550° C.

10. The method of claim 1, wherein the first time period and the third time period are 2 hours.

11. The method of claim 1, wherein the second time period and the fourth time period are 8 hours.

12. A method of synthesizing a metathesis catalyst system comprising:
    impregnating a metal oxide onto a large pore silica support in a presence of a precursor to produce a base catalyst comprising the metal oxide, wherein the large pore silica support comprises an amorphous silica;
    calcining the base catalyst at a first temperature for a first time period and a second temperature for a second time period;
    impregnating from about 0.5 wt. % to about 2.5 wt. % of a metal oxide co-catalyst, based on a total weight of the metathesis catalyst system, onto the base catalyst to produce a doped catalyst, wherein the metal oxide co-catalyst comprises Ce, Ni, or both Ce and Ni; and
    calcining the doped catalyst at a third temperature for a third time period and a fourth temperature for a fourth time period to produce the metathesis catalyst system; and
wherein the metathesis catalyst system has one or more of a surface area of about 400 $m^2/g$ to about 800 $m^2/g$, a pore size distribution of about 3 nm to about 40 nm, and a total pore volume of at least 0.700 $cm^3/g$ to about 2.5 $cm^3/g$.

13. The method of claim 12, wherein the base catalyst comprises from about 8 wt. % to about 12 wt. % tungsten oxide, based on a total weight of the base catalyst.

14. The method of claim 12, wherein the precursor comprises ammonium metatungstate hexahydrate.

15. The method of claim 12, wherein the metal oxide co-catalyst comprises Ce.

16. The method of claim 12, wherein the metal oxide co-catalyst comprises Ni.

* * * * *